United States Patent
Ghosh et al.

(10) Patent No.: US 8,865,212 B2
(45) Date of Patent: Oct. 21, 2014

(54) STABLE PHARMACEUTICAL FORMULATION OF AN ACID LABILE COMPOUND AND PROCESS FOR PREPARING THE SAME

(75) Inventors: Pradip Ghosh, Midnapur (West) Pin (IN); Gour Mukherji, Gurgaon (IN)

(73) Assignee: Jubilant Generics Limited, Noida, Uttar Pradesh (IN)

(*) Notice: Subject to any disclaimer, the term of this patent is extended or adjusted under 35 U.S.C. 154(b) by 1162 days.

(21) Appl. No.: 12/087,085

(22) PCT Filed: Nov. 20, 2006

(86) PCT No.: PCT/IN2006/000463
§ 371 (c)(1),
(2), (4) Date: Jun. 25, 2008

(87) PCT Pub. No.: WO2007/080601
PCT Pub. Date: Jul. 19, 2007

(65) Prior Publication Data
US 2009/0022795 A1    Jan. 22, 2009

(30) Foreign Application Priority Data
Jan. 16, 2006 (IN) .............................. 114/DEL/2006

(51) Int. Cl.
*A61K 9/20* (2006.01)
*A61K 9/28* (2006.01)
*A61K 31/44* (2006.01)

(52) U.S. Cl.
CPC .............. *A61K 9/2886* (2013.01); *A61K 31/44* (2013.01)
USPC .......................................... 424/465; 424/474

(58) Field of Classification Search
CPC ..... A61K 31/44; A61K 9/2886; A61K 9/2054; A61K 9/28
USPC ..................................................... 424/465, 474
See application file for complete search history.

(56) References Cited

U.S. PATENT DOCUMENTS

| | | | |
|---|---|---|---|
| 4,786,505 A | 11/1988 | Lovgren et al. | |
| 4,853,230 A | 8/1989 | Lovgren et al. | |
| 5,035,899 A | 7/1991 | Saeki et al. | |
| 5,945,124 A * | 8/1999 | Sachs et al. | 424/472 |
| 5,997,903 A | 12/1999 | Dietrich et al. | |
| 6,274,173 B1 | 8/2001 | Sachs et al. | |
| 6,602,522 B1 | 8/2003 | Chen et al. | |
| 2004/0191318 A1 * | 9/2004 | Touchot | 424/489 |
| 2006/0024362 A1 | 2/2006 | Seth | |

FOREIGN PATENT DOCUMENTS

| | | | | |
|---|---|---|---|---|
| EP | 0 496 437 | | 7/1992 | |
| EP | 0496437 | | 7/1992 | |
| EP | 0589981 | | 4/1994 | |
| WO | WO2005/009410 | | 2/2005 | |
| WO | WO 2006/111853 A2 * | | 10/2006 | ......... A61K 31/4439 |

* cited by examiner

*Primary Examiner* — Aradhana Sasan
(74) *Attorney, Agent, or Firm* — William D. Hare; McNeely, Hare & War, LLP

(57) ABSTRACT

The disclosed invention provides oral pharmaceutical formulations of an acid labile benzimidazole derivative comprising (a) a core comprising an acid labile benzimidazole derivative, (b) a seal coating layer, and (c) an enteric coating layer, wherein the core of the composition is devoid of any disintegrant.

18 Claims, 1 Drawing Sheet

A -- Reference "Zurcale" tablet
B -- Test tablet of example 1

Linear plot of mean plasma concentration of pantoprazole versus time curves after administration of reference "Zurcale" tablet and test pantoprazole tablet of example 1 to healthy, adult, human male subjects under fasting conditions.

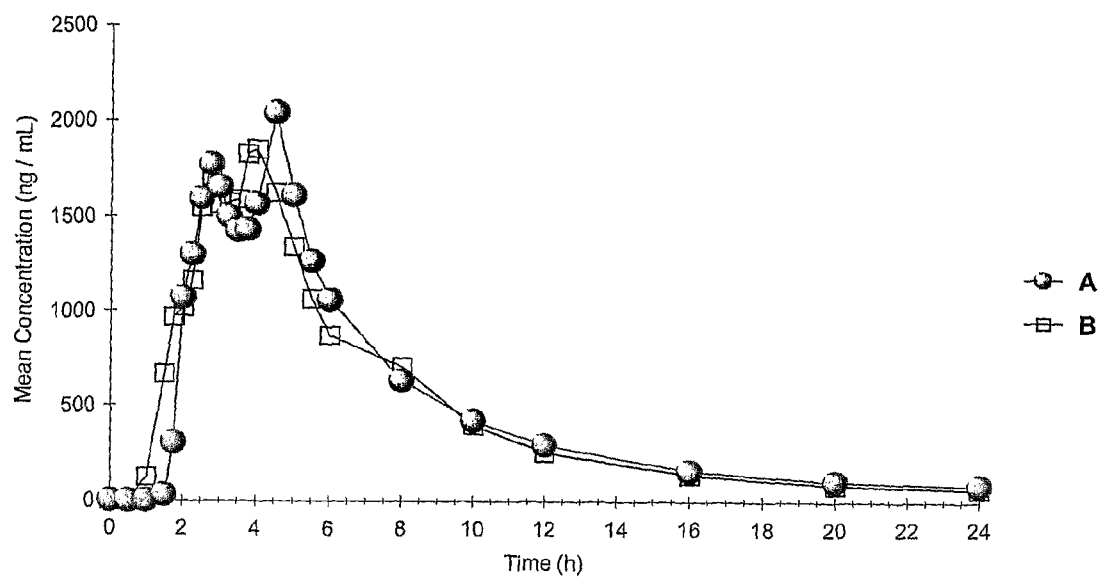
A -- Reference "Zurcale" tablet
B -- Test tablet of example 1
Linear plot of mean plasma concentration of pantoprazole versus time curves after administration of reference "Zurcale" tablet and test pantoprazole tablet of example 1 to healthy, adult, human male subjects under fasting conditions.

STABLE PHARMACEUTICAL FORMULATION OF AN ACID LABILE COMPOUND AND PROCESS FOR PREPARING THE SAME

FIELD OF THE INVENTION

This invention, in general relates to a pharmaceutical formulation of an acid labile compound and process for preparing the same. More particularly, the present invention provides a stable pharmaceutical formulation comprising a benzimidazole derivative wherein the formulation is essentially free of a disintegrant.

BACKGROUND OF THE INVENTION

The acid-labile drugs essentially comprise of substituted benzimidazole gastric anti-secretary agents, such as omeprazole, lansoprazole, pantoprazole, rabeprazole and pharmaceutically acceptable salts thereof. These agents are known proton pump inhibitors with powerful inhibitory action against secretion of gastric acid. They are indicated for the treatment of various digestive ulcers, are well known in the art and are described in U.S. Pat. No. 4,255,431.

It has been found that these benzimidazole derivatives are easily destroyed in the acid medium and thus are difficult to formulate for oral administration. Upon oral administration, the pharmaceutical composition comes in contact with gastric fluid in the stomach, which is highly acidic, leading to breakdown and loss of activity of the benzimidazole derivative.

Pharmaceutical compositions comprising acid labile drugs are protected from acidic gastric juices by an enteric coating. However most of the enteric coating materials are either themselves acidic in nature or contain acidic materials, which may react with the benzimidazole derivative and cause degradation.

The stability problems associated with benzimidazole compounds are well recognized in the prior art, which teaches various approaches for preparing stable formulations containing benzimidazole compounds. One of the most common approaches utilized to stabilize benzimidazole compounds, is the use of an alkaline core, followed by a separating layer and finally an enteric layer. It is also stated in the art that the use of fillers and binders in the core reduces the stability problems associated with benzimidazole derivatives. Several prior art documents describe such compositions that are suitable for oral administration of acid-labile substances.

Lovgren et al., in U.S. Pat. No. 4,786,505, describe a stable pharmaceutical preparation of omeprazole that resist acid attack, but dissolves rapidly in neutral or alkaline media. Particles of omeprazole are mixed with water-soluble alkaline-reacting substances and the particles are coated with a "separating layer" that acts as a pH-buffering zone to prevent contact of the drug and acidic groups that are present in the final enteric coating material which forms the outermost coated layer.

U.S. Pat. No. 4,853,230 assigned to Aktiebolaget Hassle, discloses a pharmaceutical preparation containing an acid labile compound together with an alkaline reacting compound or an alkaline salt of an acid labile compound optionally together with an alkaline compound as the core material, one or more seal coating layers comprising inert reacting compounds which are soluble or rapidly disintegrating in water, or polymeric, water soluble film forming compounds, optionally containing pH-buffering alkaline compounds and then are coated with an enteric film-forming material.

U.S. Pat. No. 5,997,903 assigned to Byk Golden Lomberg Chem Fab, covers an orally administrable medicament in pellet or tablet form comprising a core in which active compound or its physiologically-tolerated salt is admixed with binder, filler, a basic inorganic compound and, optionally, a member selected from the group consisting of another tablet auxiliary and the core is coated with an inert water-soluble intermediate layer and an outer layer which is resistant to gastric juice. The patent claims pantoprazole as the active ingredient, polyvinylpyrrolidone and/or hydroxypropyl methylcellulose as the binder and mannitol as filler. According to Dietrich et al., the use of mannitol as the sole filler for tablets requires a suitable binder, which imparts adequate hardness to the core. The equivalent European Patent, EP0589981 relates to oral medicament of acid labile compounds, which have a core containing pantoprazole as an active ingredient mixed with one or more binders, fillers, optionally one or more basic physiologically tolerated inorganic compounds and other tablet auxiliaries and the core is coated with a water soluble intermediate layer, then are coated with a gastric juice resistant outer layer.

U.S. Pat. No. 5,035,899 to Saeki et al., relates to compositions of acid-unstable drugs, which are protected against contact with gastric acid. A core that contains the drug is coated first with fine particles of a material having low water solubility, then coated with enteric film forming material.

Sachs et al., in U.S. Pat. No. 6,274,173 disclosed a controlled release pharmaceutical composition that includes an acid labile proton pump inhibitor other than pantoprazole, an alkaline pellet or tablet core, at least one water insoluble intermediate layer which controlled the release of the active ingredient, and an outer enteric layer which was soluble in the intestine. The seal coating was described as controlling the release of the active ingredient and thereby the active ingredient was released in a modified release manner, i.e., part of the active ingredient was released in immediate manner and part was released in controlled manner.

U.S. Pat. No. 6,602,522 assigned to Andrx Pharmaceuticals, discloses pharmaceutical composition of omeprazole for oral administration which includes a core component containing a therapeutically effective amount of an acid-labile compound, for example, substituted benzimidazole, such as, omeprazole, an optional surface active agent, a filler, a pharmaceutically acceptable alkaline agent, a binder; and a single layer of coating on said core which comprises a layer of an enteric coating agent.

A need exists for a drug-containing dosage form in which drug substances will not be exposed to acid in the stomach, but will be rapidly released when the dosage form enters a more alkaline environment and at the same time the composition must be stable.

SUMMARY OF THE INVENTION

It is a principal object of the present invention is to provide a novel and cost effective pharmaceutical formulation of an acid labile benzimidazole derivative having better stability and effective bioavailability.

Further object of the present invention is to provide a novel pharmaceutical formulation of an acid labile benzimidazole derivative, wherein said formulation comprises a core essentially free of disintegrant, a seal coat and an enteric coat over the seal coat.

One other object of the present invention is to provide a novel pharmaceutical formulation for an acid-labile benzamidazole derivative, wherein said formulation comprises a core essentially free of disintegrant and optionally comprises a binder, a seal coat and an enteric coat over the seal coat.

Yet another object of the present invention is to provide a novel pharmaceutical formulation of an acid labile benzimidazole derivative, wherein the formulation employs a unique combination of water-soluble and water insoluble excipients, which lend certain advantages to the pharmacokinetics of the active ingredient.

Still another object of the present invention is to provide a process for preparing a novel pharmaceutical formulation of an acid labile benzimidazole derivative, wherein said formulation having better stability and effective bioavailability by selection of excipients such as to control the drug release from the interplay of said excipients, based upon their aqueous solubility and hydrophobicity.

The following embodiments further describe the objects of the present invention, however, the disclosed invention is not restricted to the particular embodiments hereinafter described and extends to cover the modifications obvious to one of ordinary skill in the art.

In a preferred embodiment, the subject formulation comprises; (a) a compressed core comprising a therapeutically effective amount of an acid-labile benzimidazole derivative, a filler and a pharmaceutically acceptable alkaline agent; (b) at least a single layer of water-soluble sealcoating on said compressed core; and (c) at least a single layer of enteric coating on said sealcoating layer, wherein the compressed core is devoid of any disintegrant.

In another preferred embodiment, the subject formulation comprises; (a) a compressed core comprising a therapeutically effective amount of an acid-labile benzimidazole derivative, a filler and a pharmaceutically acceptable alkaline agent; (b) at least a single layer of water-soluble sealcoating on said core; and (c) at least a single layer of enteric coating on said sealcoating layer, wherein the compressed core is devoid of any disintegrant and optionally comprises a binder.

Another embodiment of the present invention provides a method for the preparation of pharmaceutical formulation of an acid labile benzimidazole derivative, comprising the step of forming a compressed core comprising an acid labile benzimidazole derivative, a filler, a pharmaceutically acceptable alkaline agent, optionally containing a binder and essentially free of disintegrant, seal coating said compressed core, followed by coating with an enteric coating agent which provides delayed release properties to the benzimidazole formulation, essential for gastric stability of the acid labile benzimidazole derivative.

In the pharmaceutical dosage form or formulation of the present invention, the acid labile benzimidazole derivatives include but are not limited to, omeprazole, lansoprazole, pantoprazole, rabeprazole, timoprazole or picoprazole or their pharmaceutically acceptable salts, solvates or hydrates. The preferred benzimidazole derivative for the composition of the present invention is pantoprazole or its pharmaceutically acceptable salts, solvates or hydrates.

Another embodiment of the composition of the present invention comprises fillers, alkaline agents, glidants, antiadherents, lubricants, seal-coating agents, enteric coating agents, plasticizers, coloring aids, opacifiers and solvents.

BRIEF DESCRIPTION OF THE DRAWING

FIG. 1 is a graphical depiction of bioavailabilty of commercially available pantoprazole delayed release tablet "Zurcale" from Altana Pharma and pantoprazole delayed release tablet of example 1.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The term "acid labile benzimidazole" as used herein refers to benzimidazole compounds of therapeutic interest whose half life is less than 10 minutes in an aqueous solution that has a pH less than 4, for example pantoprazole, lansoprazole, rabeprazole and the like.

The term "delayed release tablet" as used herein refers to a solid dosage, which releases a drug (or drugs) at a time other than promptly after administration. For the purpose of this invention enteric-coated articles are delayed release dosage forms.

Unless otherwise stated the weight percentages expressed herein are based on the final weight of the composition or formulation.

The term $C_{max}$ as used herein means the maximum plasma/blood pantoprazole concentration achieved after oral administration of the pantoprazole delayed release tablet.

The term $T_{max}$ as used herein means the time at which maximum plasma concentration of pantoprazole is achieved.

The term AUC (area under the curve) as used herein indicates the total amount of pantoprazole absorbed by the bloodstream in a predetermined time, generally 24 hours. AUC is a measure of bioavailability, which is calculated by integrating plasma concentration levels of pantoprazole with respect to time.

$AUC_{0-t}$ as used herein indicates the area under the plasma concentration of pantoprazole versus time curve from time zero to the last measured concentration as calculated by linear trapezoidal method.

$AUC_{0-\infty}$ as used herein indicates area under the plasma concentration of pantoprazole versus time curve from time zero to infinity.

The present invention describes pharmaceutical composition of an acid labile benzimidazole derivative comprising a core, a subcoat of water soluble inert coating agent, followed by a film of an enteric coating agent on the subcoat, the core containing a benzimidazole derivative, a filler, a pharmaceutically acceptable alkaline agent and optionally containing a binder and essentially free of disintegrant.

Surprisingly, it is found by the inventors of the present invention that in compositions of benzimidazole compounds, particularly pantoprazole compositions, addition of binder is optional and use of disintegrant essentially can be avoided. Still the resulting product has good binding and disintegrating properties along with excellent storage stability. The composition of the present invention despite the absence of disintegrant exhibit bioequivalence with the innovator's marketed tablet of pantoprazole sodium sesquihydrate having substantial amount of the disintegrant. Wyeth Pharmaceutical Limited markets pantoprazole sodium sesquihydrate tablets in USA under the brand name Protonix. Altana Pharma under the brand name Protium and Zurcale, markets pantoprazole tablets in European countries.

In one preferred embodiment the present invention discloses a novel formulation, which is (1) essentially free of a disintegrant in an acid-labile compound composition, (2) optionally containing a binder and (3) in absence of disintegrant, the composition controls the drug release from the interplay of other formulation excipients, based upon their aqueous solubility and hydrophobicity.

Tablet Core

The core of the pharmaceutical composition of the present invention comprises a benzimidazole derivative as active ingredient, fillers, alkaline agents, lubricants and glidants.

In one embodiment of the composition of present invention, benzimidazole derivatives include but are not limited to, omeprazole, lansoprazole, pantoprazole, rabeprazole, timoprazole or picoprazole or its pharmaceutical acceptable salts, solvates or hydrates. The preferred benzimidazole derivative for the composition of the present invention is pantoprazole or its pharmaceutical acceptable salts, solvates or hydrates.

The benzimidazole derivatives of the present invention are used in an amount of about 10-30% by weight.

The fillers of the present invention are selected from various examples of polyols. Examples of polyols suitable for composition of the present invention include but are not limited to mannitol, sorbitol, xylitol, lactiltol, erythritol or maltitol or combination thereof. The preferred filler for the composition of the present invention is mannitol. Mannitol used in the present invention is commercially available under the brand name Mannitol M 25 from Roquette, France. Preferably, filler is used in an amount of about 40-70% by weight.

The unlimiting examples of lubricants used in the core of the pharmaceutical composition of the present invention include calcium stearate, magnesium stearate, zinc stearate, light mineral oil, glyceryl behenate, polyethylene glycol, sodium stearyl fumarate, stearic acid, and talc. The preferred lubricant is calcium stearate. Calcium stearate is commercially available from Ferro, Portugal under the brand name Calcium stearate VG. Preferably, lubricant is used in an amount of 0.2-5% by weight.

The unlimiting examples of glidants used in the core of the pharmaceutical composition of the present invention include calcium silicate, magnesium silicate, colloidal silicon dioxide and talc. The preferred glidant is talc. Talc is commercially available from Luzenac, Italy. Preferably the glidants are used in amounts of about 0.5-10% by weight.

In order to provide a microenvironment of pH above 7 around the acid labile benzimidazole derivative active ingredient, the pharmaceutical composition of the present invention comprises an alkaline agent. Examples of alkaline agents include but are not limited to pharmacologically tolerated alkali metal, alkaline earth metal or metal salts of weak acids such as sodium carbonate which can be anhydrous or hydrous, calcium carbonate and magnesium carbonate and the pharmacologically tolerated hydroxides and oxides of alkaline earth and earth metals such as magnesium hydroxide and magnesium oxide. The preferred alkaline agent for the composition of the present invention is anhydrous sodium carbonate. Anhydrous sodium carbonate is commercially available from Dr. Paul Lohmann, Germany. Preferably, the alkaline agent is used in amount of about 2-10% by weight.

The optional binder for the composition of the present invention can be selected from the group comprising hydroxypropyl cellulose, polyvinylpyrrolidone, methylcellulose, and microcrystalline cellulose. Hydroxypropyl cellulose is commercially available under the brand name Klucel EXF Pharm from Aqualon-Hercules, USA. The preferred optional binder for the composition of the present invention is hydroxypropyl cellulose. Preferably, the binder is optionally used in amounts of about 0-5% by weight.

Seal Coating Layer

The water-soluble sealcoating layer of the present composition is designed to disintegrate rapidly in an aqueous medium. The seal coating layer of the present invention comprises at least one water-soluble polymer selected from the group comprising of polyethylene glycol, polyvinylpyrrolidone, hydroxypropylcellulose, and hydroxypropyl methylcellulose. The preferred polymer for the seal coating layer of the present invention is low viscosity hydroxypropyl methylcellulose. Hydroxypropyl methylcellulose, having viscosity of three centipoise, is commercially available from ShinEtsu, Japan, under the brand name Methocel E3 and Pharmacoat 603. Preferably, the water-soluble polymers comprising the seal coating layer are used in amounts of about 1-10% by weight.

The seal coating layer may further comprise other additives like plasticizers, such as, propylene glycol, triacetin, polyethylene glycol, tributyl citrate or triethyl citrate and anti-tacking agents, such as, calcium silicate, magnesium silicate, colloidal silicon dioxide or talc. The preferred plasticizer for the seal coating layer is polyethylene glycol 400. Polyethylene glycol 400 is commercially available from BASF Pharma, Germany, under the brand name Lutrol E 400. Preferred anti-tacking agent is talc, which is commercially available from Luzenac, Italy. Preferably, plasticizers and anti-tacking agents are used in amounts of about 0.1-5% and 0.2-5% by weight, respectively.

Apart from plasticizers and anti-tacking agents as mentioned above, the seal coating layer may optionally contain buffers, colorants, opacifiers, surfactants or bases, which are known to those skilled in the art.

The seal coating layer is applied on the core using any conventional coating equipment. However, more sophisticated devices like fluidized bed coater can also be used conveniently for producing the seal coating layer on the core.

Enteric Coating Layer

The enteric layer for the compositions of the present invention refers to one or more layers comprising enteric polymer produced on the seal coating layer. Enteric layer is soluble in intestinal fluid and resistant to gastric fluids. The enteric layer helps to protect the acid labile benzimidazole derivative active ingredient from acidic degradation while the dosage form transits the stomach.

The enteric layer for the composition of the present invention comprises one or more enteric polymers, plasticizers, anti-tacking agents, opacifiers, colorants, and flavoring agents.

The enteric polymers for the compositions of the present invention can be selected from the group comprising of cellulose phthalates and derivatives thereof, cellulose acetate phthalate, hydroxypropyl methylcellulose phthalate, and polyvinyl phthalate acetate and methacrylic acid copolymers. The preferred enteric polymer for the composition of the present invention is methacrylic acid copolymers. Anionic polymers with metacrylic acid as a functional group are excellent enteric polymers and are commercially available from Degussa, Germany, under the brand names Eudragit®L 100-55 (powder form), Eudragit® L30 D-55 (30% aqueous dispersion of Eudragit®L 100-55), Eudragit L100 (powder form) and Eudragit®S 100 (powder form). Still more preferred enteric polymer for the composition of the present invention is Eudragit® L30 D-55 which is an aqueous dispersion of an anionic copolymer based on methacrylic acid and ethyl acrylate. Preferably, enteric polymer is used in an amount of about 5-15% by weight.

The unlimiting examples of plasticizers include propylene glycol, triacetin, polyethylene glycol, tributyl citrate or triethyl citrate. The preferred plasticizer is triethyl citrate. Triethyl citrate is commercially available under the brand name Citroflex from Pfizer, USA. Triethyl citrate is also commercially available from Morflex Inc, USA. Preferably, plasticizer is used in an amount of about 1-5% by weight.

The unlimiting examples of anti-tacking agents include calcium stearate, magnesium silicate, silicon dioxide colloidal and talc. The preferred anti-tacking agent is talc. Talc is commercially available from Luzenac, Italy. Preferably, anti-tacking agent is used in amounts of about 0.5-10% by weight.

Opacifier is selected from various ingredients known to those skilled in the art including, for example, titanium dioxide. The preferred opacifier for the enteric coating layer is titanium dioxide. Titanium dioxide is commercially available from Kronos Germany under the brand name Titanium dioxide Kronos 1170. Preferably, the opacifier is used in amounts of about 1-5% by weight.

The unlimiting examples of colorants of the enteric layer include caramel, ferric oxide red, ferric oxide yellow, F D C yellow no. 6 and black. The preferred colorant for the enteric layer is F D C yellow no. 6. F D C yellow no. 6 is commercially available from Colorcon, USA. Preferably, colorant is used in amount of about of 0-5% by weight.

Enteric coating layer is applied on the seal coating layer using any conventional coating equipment. However, more sophisticated devices like fluidized bed coater can also be used conveniently for applying the enteric coating layer of aqueous dispersion of enteric polymers on the seal coating layer of the core.

Another embodiment of the present invention also provides a method for the preparation of pharmaceutical composition of an acid labile benzimidazole derivative active ingredient, comprising the steps of (1) dry mixing benzimidazole derivative active ingredient with diluent and 50% quantity of alkaline agent, (2) granulating the resultant blend as obtained in (1) with aqueous solution of sodium carbonate, (3) passing the wet mass as obtained in step (2) through suitable size sieve and drying the granulates in a suitable drying equipment, (4) passing the resultant granules through a suitable size mesh and mixing the same with lubricants and glidants, (5) compressing the lubricated granules into tablet core, (6) dissolving the water soluble polymer of low viscosity in water and incorporating the plasticizer and anti-tacking agent in the aqueous solution of polymer, (7) seal coating the core as obtained in step (5) with the coating solution as obtained in step (6) using suitable coating equipment, (8) dissolving or diluting the enteric polymer in water and adding plasticizer, anti-tacking agent, colorant and opacifier into the said solution or dispersion, and finally (9) enteric coating the subcoated core in the suitable coating apparatus.

The process for the invention makes it possible to prepare a pharmaceutical composition of a benzimidazole derivative wherein the composition is optionally containing binder and essentially free of disintegrant and still has good storage stability.

The composition of the invention can be formulated into different physical forms like conventional tablets, beads and mini tablets having dimensions ranging from 1-6 mm.

The following non-limiting examples illustrate specific embodiments of the present invention. They are, however not intended to be limiting the scope of the present invention in any way.

Example 1

Pantoprazole Delayed Release Tablets

TABLE 1

Core Tablet Composition

| S. No. | Ingredients | Qty (mg/tab) |
|---|---|---|
| 1. | Pantoprazole sodium sesquihydrate | 45.20 |
| 2. | Mannitol 25 | 101.60 |
| 3. | Sodium carbonate | 10.00 |
| 4. | Talc | 0.80 |
| 5. | Calcium stearate | 0.80 |
| 6. | Purified Water* | 22.00 |
|  | Total | 158.4 |

*Not present in final formulation

Procedure:

1. Pantoprazole sodium sesquihydrate, mannitol and sodium carbonate (5 mg) were passed through suitable mesh and mixed together.
2. Sodium carbonate (5 mg) was dissolved in water and the resultant dispersion was used for the granulation of mixture obtained in step 1.
3. Granules formed were passed through suitable mesh and dried in a suitable drier.
4. Dried granules were passed through suitable mesh and mixed with talc and calcium stearate.
5. Lubricated granules were compressed into tablet cores.

The tablet cores as produced above had good processing and handling properties. The physical characteristics of the core tablets as obtained in step 5 above were within the established pharmacopeial limits as mentioned in table 2 below.

TABLE 2

Physical Characteristics of Pantoprazole Core Tablet

| Tablet core characteristic | Observed value |
|---|---|
| Weight | 158.1 mg |
| Hardness | 4-5 kP |
| Disintegration Time | 4-5 minutes |
| Friability | 0.22% |

TABLE 3

Seal Coating Composition

| S. No. | Ingredients | Qty (mg/tab) |
|---|---|---|
| 1 | HPMC E3 | 6.914 |
| 2 | Talc | 2.30 |
| 3 | PEG 400 | 1.382 |
| 4 | Spectracol F D C yellow no. 6 lake | 0.0043 |
| 5 | Purified Water* | q.s |
|  | Total | 169.00 |

*Not present in final formulation

Procedure:

6. Tablet cores obtained in step 5 were seal coated with coating dispersion prepared from above mentioned composition (table 3), in a conventional coating pan. The coating dispersion was prepared as follows: (i) HPMC E3 was dissolved in water; (ii) PEG 400 was added in solution of step (i); (iii) talc and Spectracol F D C yellow no. 6 lake were dispersed in a portion of water and the same dispersion was added into dispersion of (ii) with gradual stirring.

TABLE 4

Enteric Coating Composition

| S. No. | Ingredients | Qty (mg/tab) |
|---|---|---|
| 1 | Eudragit L30D-55 (solid content) | 12.90 |
| 2 | Triethyl citrate | 1.295 |
| 3 | Talc | 1.943 |
| 4 | Spectracol F D C yellow no. 6 lake | 0.006 |
| 5 | Titanium dioxide | 0.648 |
| 6 | Purified Water* | q.s |
|  | Total | 185.792 |

*Not present in final formulation

Procedure:
7. Seal coated tablets obtained in step 6 were enteric coated with the coating dispersion prepared from above mentioned composition (table 4), in a conventional coating pan. The enteric coating dispersion was prepared as follows: (i) talc, Spectracol F D C yellow no. 6 lake and titanium dioxide were dispersed in water and homogenized for five minutes; (ii) triethyl citrate was added into Eudragit L30D-55; (iii) dispersion of (i) was added into dispersion of (ii) under gradual stirring.

Example 2

Pantoprazole Delayed Release Tablets

TABLE 5

Core Tablet Composition

| S. No. | Ingredients | Qty (mg/tab) |
|---|---|---|
| 1. | Pantoprazole sodium sesquihydrate | 45.20 |
| 2. | Mannitol 25 | 99.00 |
| 3. | Sodium carbonate | 10.00 |
| 4. | Hydroxypropylcellulose (Klucel EXF) | 0.8 |
| 5. | Talc | 3.00 |
| 6. | Calcium stearate | 1.92 |
| 7. | Purified water* | 35.00 |
| | Total | 159.92 |

*Not present in final formulation

Procedure:
1. Part of sodium carbonate (5 mg) was dissolved in purified water
2. Pantoprazole sodium sesquihydrate, mannitol 25, appropriate quantity of sodium carbonate (5 mg), and hydroxypropylcellulose (Klucel EXF) were passed through suitable mesh and mixed together.
3. Mixture of step 2 was granulated with solution of step 1.
4. The granules were dried at appropriate temperature in a suitable dryer.
5. The dried granules were passed through suitable mesh size and lubricated.
6. The lubricated granules were compressed into tablet cores.

The tablet cores as produced above had good processing and handling properties. The physical characteristics of the core tablets as obtained in step 6 above were within the established pharmacopeial limits as mentioned in table 6 below.

TABLE 6

Physical Characteristics of Pantoprazole Core Tablet

| Tablet core characteristic | Observed value |
|---|---|
| Weight | 160 mg |
| Hardness | 7-8 kP |
| Disintegration Time | 7-8 minutes |
| Friability | 0.12% |

TABLE 7

Seal Coating Composition

| S. No. | Ingredients | Qty (mg/tab) |
|---|---|---|
| 1 | HPMC 3 cps | 5.214 |
| 2 | Talc | 1.738 |
| 3 | PEG 400 (Polyethylene glycol 400) | 1.043 |
| 4 | Spectracol F D C yellow no. 6 lake | 0.0043 |
| 5 | Purified Water* | q.s |
| | Total | 167.919 |

*Not present in final formulation

Procedure:
7. Tablet cores obtained in step 6 were seal coated with coating dispersion prepared from above mentioned composition (Table 7), in a conventional coating pan. Seal coating dispersion was prepared as follows: (i) HPMC 3 cps was dispersed in water; (ii) PEG 400 was added to the dispersion of (i); (iii) talc and Spectracol F D C yellow no. 6 lake were dispersed in sufficient quantity of water and the dispersion was homogenized for five minutes; (iv) dispersion of (iii) was added to dispersion of (ii) under gradual stirring.

TABLE 8

Enteric Coating Composition

| S. No. | Ingredients | Qty (mg/tab) |
|---|---|---|
| 1 | Eudragit L30D-55 (solid content) | 12.91 |
| 2 | Triethyl citrate | 1.296 |
| 3 | Talc | 1.944 |
| 4 | Titanium Dioxide | 0.648 |
| 5 | Spectracol F D C yellow no. 6 lake | 0.006 |
| 6 | Purified Water* | q.s |
| | Total | 184.72 |

*Not present in final formulation

Procedure:
8. Seal coated tablets obtained in step 7 were enteric coated with the enteric coating dispersion as prepared from above mentioned composition (table 8), in a conventional coating pan. The enteric coating dispersion was prepared as follows: (i) Talc, Spectracol F D C 6 yellow lake and titanium dioxide were dispersed in water and homogenized for five minutes; (ii) triethyl citrate was added into Eudragit L30D-55; (iii) dispersion of (i) was added into dispersion of (ii) under gradual stirring.

Example 3

Lansoprazole Delayed Release Tablets

TABLE 9

Core Tablet Composition

| S. No. | Ingredients | Qty (mg/tab) |
|---|---|---|
| 1. | Lansoprazole | 30.0 |
| 2. | Mannitol 25 | 100.5 |
| 3. | Sodium carbonate | 10.0 |
| 4. | Purified Water* | 30.0 |
| 5. | Talc | 3.00 |
| 6. | Calcium stearate | 1.5 |
| | Total | 145 |

Manufacturing Procedure:
1. Lansoprazole, appropriate quantities of mannitol 25 (5 mg) and sodium carbonate (5 mg) were passed through suitable sieve and blended together.
2. Rest of the quantity of mannitol (5 mg) and sodium carbonate (5 mg) were dissolved in purified water.
3. Mixture of step 1 was granulated with solution of step 2.
4. The granules were dried at appropriate temperature in a suitable dryer.
5. The dried granules were passed through suitable mesh size and lubricated
6. The lubricated granules were compressed into tablet core.

The tablet core as produced above had good processing and handling properties. The physical characteristics of the core tablet as obtained in step 6 above were within the established pharmacopeial limits as mentioned in the table 10 below.

TABLE 10

Physical Characteristics of Lansoprazole Core Tablets

| Tablet core characteristics | Observed value |
| --- | --- |
| Weight | 145 mg |
| Hardness | 4-5 kP |
| Disintegration Time | 2-3 minutes |
| Friability | 0.24% |

TABLE 11

Seal Coating Composition.

| S. No. | Ingredients | Qty (mg/tab) |
| --- | --- | --- |
| 1 | HPMC 3 cps | 4.73 |
| 2 | Talc | 1.58 |
| 3 | PEG 400 (Polyethylene glycol 400) | 0.95 |
| 4 | Spectracol F D C yellow no. 6 lake | 0.003 |
| 5 | Purified Water* | q.s |
| | Total | 152.26 |

*Not present in final formulation

Procedure:
7. Tablet cores obtained in step 6 were seal coated with seal coating dispersion prepared from above mentioned composition (table 11), in a conventional coating pan. Seal coating dispersion was prepared in the same manner as described in example 1.

TABLE 12

Enteric Coating Composition

| S. No. | Ingredients | Qty (mg/tab) |
| --- | --- | --- |
| 1 | Eudragit L30D-55 (solid content) | 11.70 |
| 2 | Triethyl citrate | 1.174 |
| 3 | Talc | 1.762 |
| 4 | Titanium dioxide | 0.587 |
| 5 | Spectracol F D C yellow no. 6 lake | 0.005 |
| 6 | Purified Water* | q.s. |
| | Total | 167.48 |

*Not present in final formulation

Procedure:
8. Seal coated tablets obtained in step 7 were enteric coated with the enteric coating dispersion prepared from above mentioned composition (table 12), in a conventional coating pan. The enteric coating dispersion was prepared in the same manner as described in example 1.

Example 4

Rabeprazole Delayed Release Tablets

TABLE 13

Core Tablet Composition

| S. No. | Ingredients | Qty (mg/tab) |
| --- | --- | --- |
| 1. | Rabeprazole sodium | 20.0 |
| 2. | Mannitol | 54.2 |
| 3. | Sodium carbonate | 5.0 |
| 5. | Talc | 0.4 |
| 6. | Calcium stearate | 0.4 |
| 7. | Purified Water* | q.s |
| | Total | 80.0 |

Manufacturing Procedure:
1. Rabeprazole Sodium, mannitol and sodium carbonate (2.5 mg) were passed through suitable sieve and blended together.
2. Rest of the quantity of sodium carbonate (2.5 mg) was dissolved in purified water.
3. Mixture of step 1 was granulated with solution of step 2.
4. The granules were dried at appropriate temperature in a suitable dryer.
5. The dried granules were passed through suitable sieve.
6. The talc and calcium stearate were passed through suitable sieve and the same were mixed with granules of step 5.
7. The lubricated granules were compressed into tablet cores.

The tablet cores as produced above had good processing and handling properties. The physical characteristics of the core tablets as obtained in step 6 above were within the established pharmacopeial limits as mentioned in table 14 below.

TABLE 14

Physical Characteristics of Rabeprazole Core Tablets

| Tablet core characteristic | Observed value |
| --- | --- |
| Weight | 82 mg |
| Hardness | 6-7 kp |
| Disintegration Time | 2-2.5 minutes |
| Friability | 0.11% |

TABLE 15

Seal Coating Composition.

| S. No. | Ingredients | Qty (mg/tab) |
| --- | --- | --- |
| 1 | HPMC 3 cps | 2.61 |
| 2 | Talc | 0.87 |
| 3 | PEG 400 (Polyethylene glycol 400) | 0.52 |
| 4 | Spectracol FDC yellow no. 6 lake | 0.002 |
| 5 | Purified Water* | q.s |
| | Total | 84.00 |

*Not present in final formulations

Procedure:
8. Tablet cores obtained in step 7 were seal coated with coating dispersion prepared from above mentioned composition (table 15), in a conventional coating pan. Seal coating dispersion was prepared in the same manner as described in Example 1.

TABLE 16

Enteric Coating Composition

| S. No. | Ingredients | Qty (mg/tab) |
|---|---|---|
| 1 | Eudragit L30D-55 (solid content) | 6.45 |
| 2 | Triethyl citrate | 0.59 |
| 3 | Talc | 0.88 |
| 4 | Titanium dioxide | 0.294 |
| 5 | Spectracol F D C no. 6 yellow lake | 0.0025 |
| 6 | Purified Water* | q.s. |
| | Total | 92.22 |

*Not present in final formulations

Procedure:

9. Seal coated tablets obtained in step 8 were enteric coated with coating dispersion prepared from above mentioned composition, in a conventional coating pan. The enteric coating dispersion was prepared in the same manner as described in Example 1.

Example 5

Accelerated stability testing as per the ICH guidelines was conducted on the tablets prepared in example 1 and example 2 at temperature/relative humidity of 40®±2° C./75%±5% for 3 months. Results in terms of amount of pantoprazole present in the tablet at the end of the period of storage were analyzed by validated high performance liquid chromatography method and the same were presented in the table 17 below.

TABLE 17

Accelerated Stability Data

| | Amount of pantoprazole in the tablet | |
|---|---|---|
| Study period | Example 1 | Example 2 |
| Initial | 97.3 | 103.3 |
| After one month | 97.6 | 101.2 |
| After two months | 94.9 | 97.9 |
| After three months | 94.3 | 98.2 |

Example 6

Bioavailabilty of Delayed Release Pantoprazole Formulation

This example demonstrates the ability of formulation of example 1 (labeled amount 40 mg pantoprazole) to provide bioavailabilty of pantoprazole, which is comparable to the bioavailabilty provided by Zurcale® (labeled amount 40 mg pantoprazole) as determined by the area under the curve (AUC) and $C_{max}$. Zurcale is marketed by Altana pharma in European countries.

This example describes an in-vivo study, which measured plasma pantoprazole concentrations achieved after oral administration of reference Zurcale® tablet and test pantoprazole tablet formulation of example 1. The in-vivo study was carried out on 12 healthy adult male subjects under fasting condition. Plasma pantoprazole was determined over a 24-hour period, after a single oral administration of the respective formulations. Each individual was administered each of the two formulations in a cross-over design. The study was completed over two consecutive weeks and there was a washout period of 3 days between administrations of the two formulations. Individual plasma levels were measured at pre-determined times utilizing a validated assay method employing LC-MS/MS instrumentation. A commercially available statistical software programme known as SAS (SAS institute Inc., USA. Version 9.1.3) was used to evaluate plasma concentration values derived at each time point and to determine the area under the curve (AUC) and maximum concentration ($C_{max}$) afforded by Zurcale® and the test formulation. The plasma concentration profiles have been depicted in FIG. 1. The test formulation provided bioavailabilty of pantoprazole, which was substantially equivalent to that of Zurcale®, as determined by the software program. Pharmacokinetic parameters for both reference and test formulation have been shown in table 18.

TABLE 18

Pharmacokinetic Data

| Parameter | Reference Product (Zurcale®) - R | Test (Formulation (Example 1) - T | T/R ratio | 90% confidence interval (test vs reference) |
|---|---|---|---|---|
| $AUC_{0-24}$ ng · h./ml | 8328.548 | 8164.935 | 0.98 | 89.01-114.09 |
| $AUC_{0-\infty}$ ng · h./ml | 8575.267 | 8336.586 | 0.97 | 92.81-103.56 |
| $C_{max}$ ng/ml | 3260.195 | 3285.421 | 1.00 | 91.85-102.89 |
| $T_{max}$ | 3.015 | 3.014 | 0.99 | |

In view of the above it is clearly evident that formulation of the invention importantly provide bioavailabilty of pantoprazole, which is comparable, or bioequivalent to Zurcale®.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. A tablet formulation of an acid labile benzimidazole derivative consisting essentially of:
    (a) a compressed core comprising an effective amount of said acid labile benzimidazole derivative, a filler and an alkaline agent;
    (b) at least one water soluble seal coating layer, said water soluble seal coating layer formed of a material selected to cause rapid disintegration in aqueous medium; and
    (c) at least an enteric coating layer;
    wherein said compressed core is devoid of any disintegrant.

2. The tablet formulation as claimed in claim 1, wherein the acid labile benzimidazole derivative is selected from the group comprising pantoprazole, omeprazole, lansoprazole, rabeprazole, timoprazole and picoprazole and its pharmaceutically acceptable salts, solvates and hydrates.

3. The tablet formulation as claimed in claim 1, wherein the acid labile benzimidazole derivative is pantoprazole or its pharmaceutically acceptable salts.

4. The tablet formulation as claimed in claim 1, wherein the filler is selected from the group comprising mannitol, sorbitol, zylitol, lactitol, erythritol and maltitol.

5. A tablet formulation as claimed in claim 4, wherein the preferred filler is mannitol.

6. A tablet formulation as claimed in claim 1, wherein the alkaline agent is selected from the group comprising sodium carbonate, calcium carbonate, magnesium carbonate, magnesium hydroxide and magnesium oxide.

7. A tablet formulation as claimed in claim 6, wherein the preferred alkaline agent is sodium carbonate.

8. A tablet formulation as claimed in claim 1, wherein filler is preferably used in an amount of about 40 to 70% by weight of the core.

9. A tablet formulation as claimed in claim 1, wherein the alkaline agent is preferably used in an amount of about 2 to 10% by weight of the core.

10. A tablet formulation as claimed in claim 1, wherein the core of said formulation further comprises a lubricant, and a glidant.

11. A tablet formulation of an acid labile benzimidazole derivative consisting essentially of:
   (a) a core of said acid labile benzimidazole derivative wherein said core comprises of, by weight:
   about 10 to 30% of said benzimidazole derivative,
   about 40 to 70% of a filler,
   about 2 to 10% of an alkaline agent, wherein the alkaline agent is sodium carbonate, and wherein the core is essentially free of disintegrant,
   (b) a water-soluble seal or seal coating layer, said water soluble seal coating layer formed of a material selected to cause rapid disintegration in aqueous medium; and
   (c) an enteric coating layer.

12. A tablet formulation of pantoprazole in the form of a tablet consisting essentially of:
   (a) a core comprising pantoprazole, wherein said core comprises of, by weight:
   about 10 to 30% of said pantoprazole,
   about 40 to 70% of mannitol,
   about 2 to 10% of sodium carbonate and wherein the core is essentially free of disintegrant,
   (b) at least one water-soluble seal or seal coating layer consisting essentially of water-soluble polymers, said water soluble seal coating layer formed of a material selected to cause rapid disintegration in aqueous medium; and
   (c) an enteric coating layer.

13. A tablet formulation of an acid labile benzimidazole derivative in the form of a tablet consisting essentially of:
   (a) a core comprising said acid labile benzimidazole derivative wherein said core comprises of, by weight:
   about 10 to 30% of said benzimidazole derivative,
   about 40 to 70% of a filler,
   about 2 to 10% of an alkaline substance,
   about 0 to 1% of a binder,
   about 0.2 to 5% of a lubricant,
   about 0.5 to 10% of a glidant, and wherein the core is essentially free of disintegrant,
   (b) at least one water-soluble seal or seal coating layer consisting essentially of water-soluble polymers, said water soluble seal coating layer formed of a material selected to cause rapid disintegration in aqueous medium, and
   (c) an enteric coating layer.

14. A tablet formulation of lansoprazole in the form of a tablet comprising:
   (a) a core comprising lansoprazole wherein said core comprises by weight:
   about 10 to 30% of said lansoprazole;
   about 40 to 70% of mannitol;
   about 2 to 10% of sodium carbonate;
   about 0 to 1% of hydroxypropyl cellulose;
   about 0.2 to 5% of calcium stearate;
   about 0.2 to 5% of talc and wherein said core is essentially free of disintegrant;
   (b) a water-soluble seal or seal coating layer, said water-soluble seal coating layer formed of a material selected to cause rapid disintegration in aqueous medium; and
   (c) an enteric coating layer.

15. A tablet formulation of rabeprazole in the form of a tablet comprising:
   (a) a core comprising rabeprazole wherein said core comprises by weight:
   about 10 to 30% of said rabeprazole,
   about 40 to 70% of mannitol,
   about 2 to 10% of sodium carbonate,
   about 0 to 1% of hydroxypropyl cellulose,
   about 0.2 to 5% of calcium stearate,
   about 0.2 to 5% of talc and wherein core is essentially free of disintegrant,
   (b) a seal or seal coating layer, said seal coating layer formed of a material selected to cause rapid disintegration in aqueous medium, and
   (c) an enteric coating layer.

16. A tablet formulation as claimed in claim 1, wherein said formulation is prepared by a process comprising the steps of:
   (i) dry mixing benzimidazole derivative active ingredient with major quantity of diluent and 50% quantity of alkaline agent;
   (ii) granulating the resultant blend of step (i) with aqueous solution of sodium carbonate and small part of filler;
   (iii) passing the wet mass as obtained in step (ii) through a sieve and drying the resultant granulates;
   (iv) passing the dried granules through a sieve and mixing the same with lubricants and glidants;
   (v) compressing the lubricated granules of step (iv) into tablet core;
   (vi) dissolving the water soluble polymer of low viscosity in water and incorporating the plasticizer and antitacking agent in the aqueous solution of polymer;
   (vii) seal coating the core as obtained in step (v) with the coating solution as obtained in step (vi);
   (viii) dissolving the enteric polymer in water and adding plasticizer, colorant, anti-tacking agent and opacifier into the said solution or dispersion and finally;
   (ix) enteric coating the subcoated core with coating solution of step (viii).

17. The tablet formulation as claimed in claim 1, wherein the water-soluble seal coating layer comprises a water soluble polymer.

18. The tablet formulation as claimed in claim 17, wherein the water-soluble polymer is hydroxypropyl methyl cellulose.

* * * * *